(12) United States Patent
Ermes et al.

(10) Patent No.: US 8,768,447 B2
(45) Date of Patent: Jul. 1, 2014

(54) PROCESSING OF PHYSIOLOGICAL SIGNAL DATA IN PATIENT MONITORING

(75) Inventors: Miikka Ermes, Ruutana (FI); Mika Särkelä, Helsinki (FI)

(73) Assignee: General Electric Company, Schenectady, NY (US)

( * ) Notice: Subject to any disclaimer, the term of this patent is extended or adjusted under 35 U.S.C. 154(b) by 2014 days.

(21) Appl. No.: 11/621,199

(22) Filed: Jan. 9, 2007

(65) Prior Publication Data
US 2008/0167569 A1 Jul. 10, 2008

(51) Int. Cl.
A61B 5/04 (2006.01)
A61B 5/0476 (2006.01)
A61B 5/048 (2006.01)

(52) U.S. Cl.
CPC ............... *A61B 5/0476* (2013.01); *A61B 5/048* (2013.01)
USPC .......................................... 600/544; 600/545

(58) Field of Classification Search
USPC ................................................ 600/544–545
See application file for complete search history.

(56) References Cited

U.S. PATENT DOCUMENTS

| | | | |
|---|---|---|---|
| 6,549,804 B1 * | 4/2003 | Osorio et al. | 600/544 |
| 6,658,287 B1 | 12/2003 | Litt et al. | |
| 2003/0158587 A1 | 8/2003 | Esteller et al. | |
| 2005/0085744 A1 | 4/2005 | Beverina et al. | |
| 2005/0137494 A1 * | 6/2005 | Viertio-Oja | 600/544 |

FOREIGN PATENT DOCUMENTS

| | | |
|---|---|---|
| WO | 0010455 A1 | 3/2000 |
| WO | 2006066337 A1 | 6/2006 |

OTHER PUBLICATIONS

U.S. Appl. No. 11/617,151, filed Dec. 28, 2006, The General Electric Company.
Sarkela M. et al. *Automatic analysis and monitoring of burst suppression in anesthesia*, Journal of Clinical Monitoring and Computing. 2002; 17:125-134.
Young GB, McLachlan RS, Kreeft JH, Demelo JD: *An Electroencephalographic Classification for Coma*, Can. J. Neurol. Sci. 1997; 24:320-3259.
Netherlands Search Report dated Dec. 22, 2008.

* cited by examiner

*Primary Examiner* — Michael D'Angelo
(74) *Attorney, Agent, or Firm* — Andrus Intellectual Property Law, LLP (57) ABSTRACT

The invention relates to processing of physiological signal data in patient monitoring. In order to alleviate the problems caused by suppression waveforms in the analysis of physiological signal data, measurement data is derived from a segment of the time series of physiological signal data and valid measurement data is collected from the derived measurement data, thereby to form a set of valid measurement data. The collecting includes selecting measurement data that fulfills at least one predetermined threshold condition. Furthermore, at least a portion of the set of valid measurement data is supplied to a further processing stage when the amount of collected measurement data in the set is at least at a predetermined level. The deriving and collecting may be repeated for consecutive segments of the time series, in which case the supplying is performed for at least some of the consecutive segments of the time series.

23 Claims, 6 Drawing Sheets

PROCESSING OF PHYSIOLOGICAL SIGNAL DATA IN PATIENT MONITORING

FIELD OF THE INVENTION

The present invention relates generally to the processing of physiological signal data. More particularly, the invention relates to the alleviation of the effects caused by so-called suppression waveforms in patient monitoring. The invention finds a typical application in connection with automatic detection of epileptiform activity in EEG signal data obtained from a patient. Epileptiform activity here refers to signal waveforms or patterns which are typical in epilepsy and which may also be associated with an increased risk of epileptic seizures.

BACKGROUND OF THE INVENTION

Electroencephalography (EEG) is a well-established method for assessing brain activity. When measurement electrodes are attached on the skin of the skull surface, the weak biopotential signals generated in brain cortex may be recorded and analyzed. The EEG has been in wide use for decades in basic research of the neural systems of the brain as well as in the clinical diagnosis of various central nervous system diseases and disorders.

The EEG signal represents the sum of excitatory and inhibitory potentials of large numbers of cortical pyramidal neurons, which are organized in columns. Each EEG electrode senses the average activity of several thousands of cortical pyramidal neurons.

The EEG signal is often divided into four different frequency bands: Delta (0.5-3.5 Hz), Theta (3.5-7.0 Hz), Alpha (7.0-13.0 Hz), and Beta (13.0-32.0 Hz). In an adult, Alpha waves are found during periods of wakefulness, and they may disappear entirely during sleep. Beta waves are recorded during periods of intense activation of the central nervous system. The lower frequency Theta and Delta waves reflect drowsiness and periods of deep sleep.

Different derangements of internal system homeostasis disturb the environment in which the brain operates, and therefore the function of the brain and the resulting EEG are disturbed. The EEG signal is a very sensitive measure of these neuronal derangements, which might be reflected in the EEG signal either as changes in membrane potentials or as changes in synaptic transmission. A change in synaptic transmission occurs whenever there is an imbalance between consumption and supply of energy in the brain. This means that the EEG signal serves as an early warning of a developing injury in the brain.

According to the present state of knowledge, the EEG signal is regarded as an effective tool for monitoring changes in the cerebral state of a patient. Diagnostically, the EEG is not specific, since many systemic disorders of the brain produce similar EEG manifestations. In Intensive Care Units, for example, an EEG signal may be of critical value, as it may differentiate between broad categories of psychogenic, epileptic, metabolic-toxic, encephalopatic and focal conditions.

Figure 1:
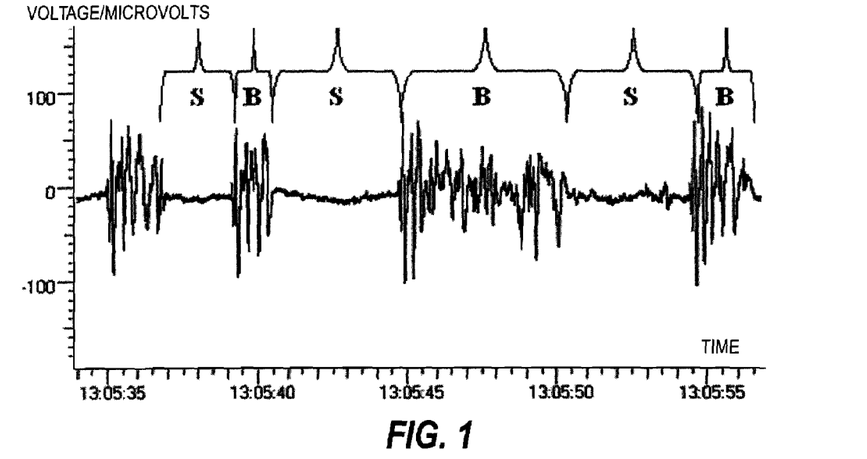
FIG. 1 illustrates exceptionally clear burst suppression waveforms in EEG.

Suppression is a peculiar EEG waveform which is relatively often encountered with various patient groups. Suppression waveforms may occur in deep anesthesia, coma, severe encephalopathy, hypothermia, hypoxic or ischemic brain injury, structural brain damage, and status epilepticus, for example. In other words, suppression may be caused by anesthetics, even to the neurologically healthy patients, or by (endogenous) neurological dysfunction. Suppression is often encountered in a combination of two alternating patterns: burst and suppression. The waveform of the two alternating patterns is called burst-suppression (BS). An exceptionally clear BS pattern is depicted in FIG. 1 in which EEG periods with burst waveform are indicated with B and those with suppressions with S.

Typically, burst patterns of neurologically healthy patients are sinusoidal-type waveforms, whereas burst patterns of neurologically ill patients may contain spiky waveforms resembling epileptic spikes (epileptiform activity). Although definitions vary, during suppression the EEG amplitude is generally below 10 μV and during bursts of the order of 100 μV.

Figure 2:
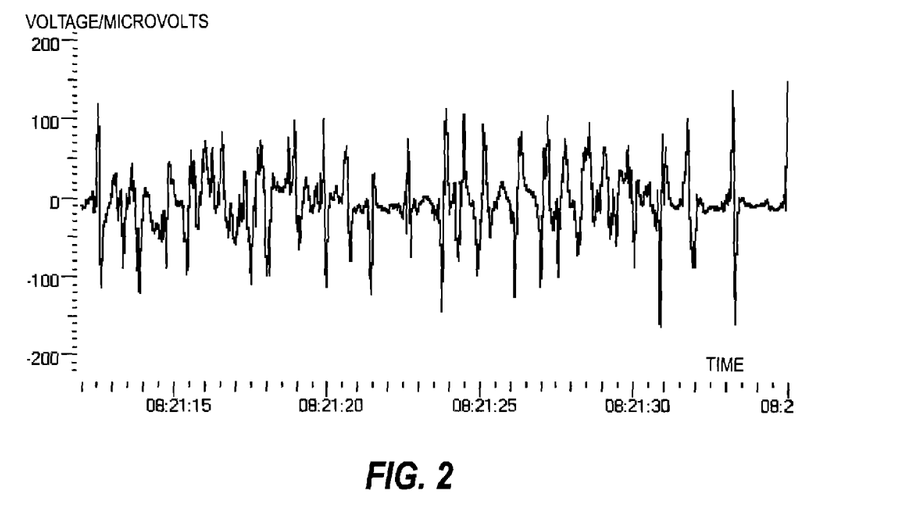
FIG. 2 illustrates an example of complex burst suppression waveforms in EEG.

Due to the rapidly changing dynamics of the EEG, burst suppression introduces many problems, which make accurate detection of burst suppression notoriously difficult. While FIG. 1 shows an example of a burst suppression pattern with clearly separable bursts and suppressions, FIG. 2 depicts an example of more commonly encountered BS waveforms, in which the discrimination of bursts and suppressions is much more difficult. Due to the difficulties, burst suppression is usually detected separately in current brain wave monitors, and a dedicated algorithm is used during burst suppression waveforms to evaluate the cerebral status of the patient during BS waveforms.

An example of an EEG monitoring device resting the detection of burst suppression is disclosed in U.S. Patent Application Publication US 2005/0137494 A1, which describes a method for determining the cerebral state of a patient using generalized spectral entropy of the EEG signal. In this method, portions of the EEG signal data containing artifacts are discarded and the remaining portions are further divided into those in which burst suppression is present and those in which burst suppression is not present. For portions of the EEG signal data in which the signal is stationary in nature and for portions in which only bursts are present, the spectral entropy is determined by their respective algorithms.

Burst suppression EEG monitoring is traditionally and most often performed by calculating a so-called burst suppression ratio (BSR), which represents the temporal proportion of suppressed EEG periods in the EEG signal. BSR calculation is available in most diagnostic EEG devices as well as in devices monitoring the depth of anesthesia. Burst suppression, as a phenomenon, has variable time characteristics. As FIG. 1 depicts, the lengths of the successive bursts and suppressions may vary. Although that information is utilized, for example, as a parameter called inter-burst-interval, which is available in some commercial EEG devices, the application area of the parameter is still unclear. BSR is typically derived over a time window of one minute, which makes it relatively insensitive to the variations in the lengths of successive bursts and suppressions, and thus also a stable indicator of the patient state. Algorithms used for the detection of burst suppression pattern are fine-tuned for the purposes of BSR calculation. Therefore, these algorithms utilize EEG data in relatively long time windows for the detection of suppressed EEG periods. For example, the time window of the algorithm described in [Sarkela M. et al. *Automatic analysis and monitoring of burst suppression in anesthesia*, Journal of Clinical Monitoring and Computing. 2002; 17:125-134.] is one second. Algorithms employing such long time windows are not able to define exact onsets and offsets of the burst patterns and, as such, are not suitable for the detailed characterization of the burst patterns. Additionally, these algorithms are not optimized to detect short epileptiform spikes occurring during suppression or short suppressions occurring during bursts, because these short duration events do not have a remarkable effect on the one-minute BSR value. As stated above, BSR utilizes only the suppressed EEG periods, which makes it inapplicable for the characterization of the burst patterns occurring between the suppressed EEG periods. Currently there are no automated methods for burst classification or characterization available.

However, there is a clear need for detailed analysis of bursts during BS waveforms, as bursts contain valuable information on the abnormalities of the brain, cf. [Young G B, McLachlan R S, Kreeft J H, Demelo J D: *An Electoencephalographic Classification for Coma*, Can. J. Neurol. Sci. 1997; 24:320-3259]. For the correct diagnosis and proper treatment it is therefore important to recognize epileptiform burst patterns from other burst parters, especially in the case of status epilepticus patients. Nevertheless, current monitors only use the relative amount of suppressions (BSR) in their analysis during BS.

The present invention seeks to alleviate the problems caused by suppression waveforms in the analysis of physiological signal data, especially EEG, by bringing about a novel mechanism for alleviating the effects of suppression waveforms in patient monitoring.

SUMMARY OF THE INVENTION

The present invention seeks to provide a novel mechanism for monitoring of physiological signal data, which allows accurate analysis of the signal even during suppression waveforms and without resorting to the error-prone detection of the suppression waveforms. The physiological signal data obtained from the patient is typically brain wave signal data, which is normally EEG signal data, but may also be magnetoencephalographic (MEG) signal data. MEG is indicative of the magnetic component of brain activity, i.e. it is the magnetic counterpart of EEG.

In the present invention, measurement data is derived from the physiological signal data obtained from a patient. As is discussed below, the measurement data here refers to a time series of a desired quantitative characteristic of the physiological signal data. The quantitative characteristic may be, for example, signal amplitude, signal power, or a wavelet coefficient. The measurement data may be determined as new physiological signal data is received, i.e. measurement data may be obtained essentially in real time. From the time series of the measurement data, valid measurement data is extracted thereby to collect a set of valid measurement data. Valid measurement data here refers to measurement data that fulfills at least one predetermined threshold condition, according to which measurement data is regarded as valid if it exceeds a first threshold level. Optionally, valid measurement data may not exceed a second threshold level higher than the first threshold level.

Thus one aspect of the invention is providing a method for processing physiological signal data. The method includes deriving measurement data from a segment of a time series of physiological signal data obtained from a subject and collecting valid measurement data from the derived measurement data, thereby to form a set of valid measurement data, wherein the collecting includes selecting measurement data that fulfills at least one predetermined threshold condition. The method further includes supplying at least a portion of the set of valid measurement data to a further processing stage when the amount of collected measurement data in the set is at least at a predetermined level.

In on-line monitoring, the set of valid measurement data may be supplied to a further processing stage only if the amount of valid measurement data in the set reaches a required level before the oldest measurement data in the set becomes obsolete, i.e. useless for representing the current state of the patient. If the oldest measurement data in the current set becomes obsolete before the required amount of valid measurement data is reached in the set, the user may be informed that the result does not any more represent the current state of the patient.

The amount of valid measurement data in the set may be increased continually as new data samples are received or stepwise so that the measurement data is first derived from a data segment of a predetermined length to see if the required amount of valid measurement data may be obtained from the said segment. If this is not the case, the data segment may be made wider to derive the measurement data from the widened segment. For example, a time window of 5 seconds may be selected first, and then, if the said time window does not provide enough valid measurement data, the time window may be widened in steps of 1 or 2 seconds until a sufficient amount of valid measurement data is derived from the corresponding data segment or until the window becomes too wide to represent the current state of the brain wave signal.

If the content of the set is increased continuously, the valid measurement data in the set may be supplied to the further processing stage immediately when the amount of valid measurement data reaches the required level. In contrast, in the stepwise increase the amount of valid measurement data normally exceeds the required level by a larger amount, since each step widening the data segment may yield a rather large amount of additional valid measurement data. Since the required level of the valid measurement data normally corresponds to the amount of data required in a further processing stage, the said amount may be selected from among the latest measurement data. In other words, if the amount of valid measurement data exceeds the required level by a certain amount, the said certain amount of oldest measurement data may be omitted.

In a typical embodiment, the invention may be utilized for detecting epileptiform activity, since the detection of epileptiform activity is especially difficult during BS waveforms. The solution of the invention enables accurate detection of epileptiform activity also during BS waveforms, without resorting to the complex and error-prone BS detection mechanisms. This is because the collection of valid measurement data eliminates the influence of suppressed brain wave signals and allows the same amount of measurement data, such as the same number of wavelet coefficients, to be supplied as input data for the subsequent processing steps, regardless of the fact that dropping a portion of the measurement data makes the corresponding time series gapped.

Consequently, the same mechanism may be used in connection with any other application in which the suppression waveforms tend to weaken the performance of the application similarly as in the context of detection of epileptiform activity. Physiological signals that may contain alternating patterns similar to burst suppression in brain wave data include electrocardiography (ECG) and electromyography (EMG) signals. In ECG, the signal segments outside the QRS complex may be considered to be suppression waveforms. In the study of action potentials in EMG, the background activity between action potentials may be regarded as suppression.

A further advantage of the method is that it enables characterization and classification of burst patterns, which supplements the information obtained from BSR monitoring. The method may be used in parallel with BSR monitoring, independently without simultaneous BSR monitoring, or as a suppression detection mechanism in connection with BSR calculation.

Another aspect of the invention is that of providing an apparatus for suppressing the effects of suppression waveforms in patient monitoring. The apparatus comprises a first data processing unit configured to derive measurement data from a segment of a time series of physiological signal data obtained from a subject and a data collection unit configured to select, from among the derived measurement data, measurement data that fulfills at least one predetermined threshold condition, thereby to form a set of valid measurement data. The apparatus further includes a data release unit configured to supply at least a portion of the set of valid measurement data to a further processing unit, when the amount of valid measurement data in the set is at least at a predetermined level.

In a still further embodiment, the invention provides a computer program for suppressing the effects of suppression waveforms in patient monitoring. The computer product comprises a first program code portion configured to derive measurement data from a segment of a time series of physiological signal data obtained from a subject, a second program code portion configured to select, from among the derived measurement data, measurement data that fulfills at least one predetermined threshold condition, thereby to form a set of valid measurement data, and a third program code portion configured to supply at least a portion of the set of valid measurement data to a further processing unit, when the amount of valid measurement data in the set is at least at a predetermined level.

Other features and advantages of the invention will become apparent by reference to the following detailed description and accompanying drawings.

BRIEF DESCRIPTION OF THE DRAWINGS

In the following, the invention and its preferred embodiments are described more closely with reference to the examples shown in FIG. 3 to 9 in the appended drawings, wherein.

DETAILED DESCRIPTION OF THE INVENTION

Below, the invention is discussed in more detail in the context of on-line analysis of brain wave signal data.

Figure 3:
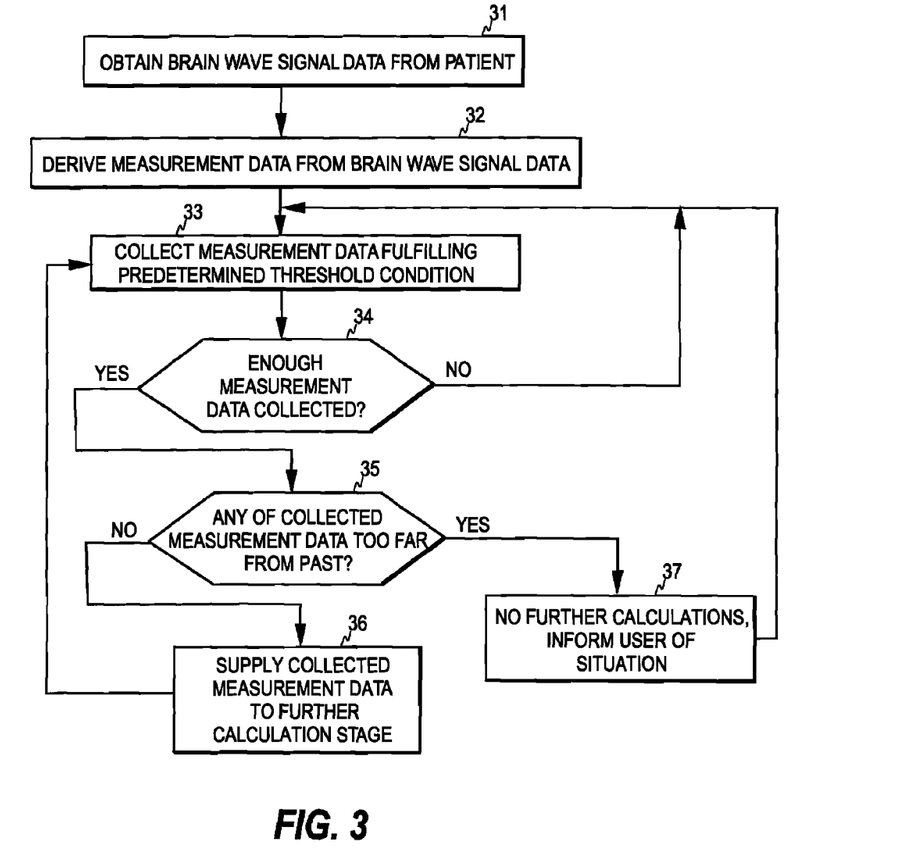
FIG. 3 is a flow diagram illustrating one embodiment of the method of the invention.

FIG. 3 is a flow diagram illustrating one embodiment of the mechanism of the invention. The raw brain wave signal data, which is typically EEG signal data obtained from a patient at step 31, is first processed (step 32) to derive a time series of measurement data from the time series of the brain wave signal data. The measurement data comprises a time series of a desired quantitative characteristic of the brain wave signal data. The quantitative characteristic may be, for example, signal amplitude, signal power, or a wavelet coefficient. New measurement data is obtained as new brain wave signal data is received from the patient, i.e. the measurement data may be obtained substantially in real time.

At step 33, the validity of the measurement data is checked by examining whether the measurement data fulfills at least one predetermined threshold condition. Only measurement data fulfilling the at least one predetermined threshold condition is collected, i.e. stored temporarily, to form a set of valid measurement data. For example, only signal samples whose amplitude exceeds a predetermined threshold level may be regarded as valid measurement data to eliminate the influence of suppressed EEG. Alternatively, the signal samples whose amplitude is between two predetermined threshold levels might be extracted to the set of valid measurement data. The use of a higher threshold eliminates the effect of artefact-contaminated EEG in further calculations. Each sample of the measurement data is provided with a time stamp that indicates the position of the corresponding brain wave signal data in the time series.

When the amount of valid measurement data in the set reaches a predetermined level, the process examines at step 35 whether any of the measurement data in the set is too far from the past. If this is not the case, the measurement data in the set is supplied to a further calculation stage (step 36), and the process jumps back to step 33 to start the collection of a new set of valid measurement data. If it is detected at step 35 that one or more of the oldest values in the set are too far from the past, no further calculations are performed based on this set, and the user is informed that the measurement does not represent the current state of the brain wave signal data (step 37). The process then jumps back to step 33 to start the collection of a new set of valid measurement data.

The calculations performed in the further calculation stage based on the valid measurement data may depend on the nature of the measurement data and on the application in question.

Figure 4:
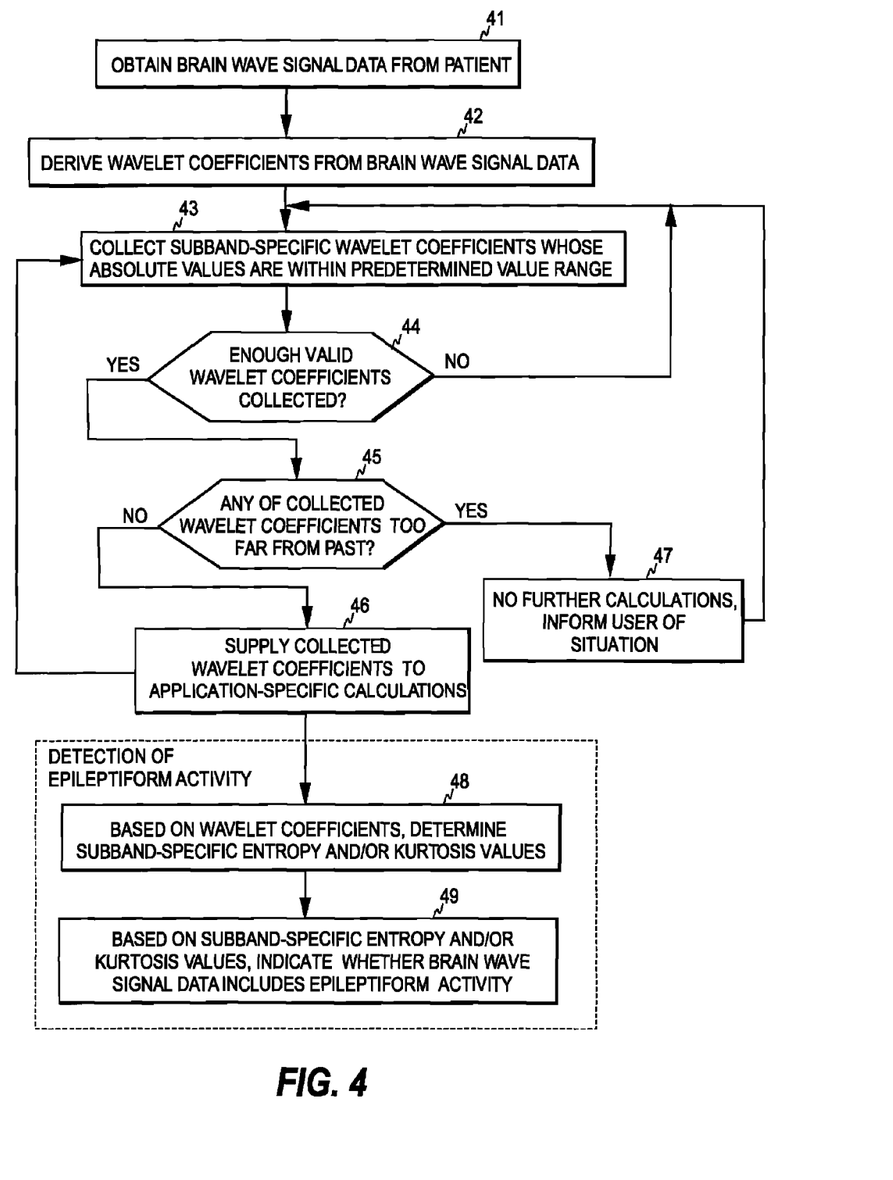
FIG. 4 is a flow diagram illustrating the method of the invention when applied in the context of monitoring epileptiform activity.

FIG. 4 illustrates the use of the above mechanism for the detection of epileptiform activity. Detection of epileptiform activity is a preferred application for the present invention, since the invention enables accurate detection of epileptiform activity even during BS waveforms, without resorting to the error-prone BS detection mechanisms that are normally needed for the analysis of the EEG. With reference to FIG. 4, in which steps 41 to 47 correspond, respectively, to steps 31 to 37 in FIG. 3, the measurement data derived (step 43) from the brain wave signal data comprises a time series of a wavelet coefficient. The wavelet coefficients may be calculated, for example, as is disclosed in Applicant's EP patent application No. 06110089.7-2305 (not public at the filing date of the present application). As is discussed in the said application, the time series may be derived for one or more sub-bands of the brain wave signal, i.e. in step 42 wavelet coefficients may be calculated for one or more subbands of the original signal and steps 43 to 49 of FIG. 4 may then be carried out for one sub-band or separately for two or more sub-bands. A discrete wavelet transform may be employed in step 42 to decompose the brain wave signal and to produce the subband-specific wavelet coefficients. Since the wavelet transform is known as such, it is not discussed in more detail in this context. The wavelet transform is also discussed in more detail in the above-referred EP patent application.

In a preliminary evaluation of one embodiment of the invention, wavelet subband entropy value of 0.87 was able to discriminate epileptiform burst suppression EEG from non-epileptiform with the sensitivity of 80%, whereas non-epileptiform burst-suppression was discriminated from epileptiform with the sensitivity of 85%. Generally, non-epileptiform burst suppression waveforms can be discriminated from epileptiform burst suppression waveforms by an appropriate wavelet subband entropy or kurtosis value.

In step 43, only the wavelet coefficients which are greater than a lower threshold value TH1 and smaller than a higher threshold value TH2 are regarded as valid measurement data and collected to the measurement data set. Furthermore, the process monitors at step 44 when the number of such valid coefficients in the set reaches a predetermined level. When this occurs, the process checks whether any of the coefficients in the set is too old (step 45). If this is not the case, the collected coefficients are supplied to a further calculation stage in which, for each subband of interest, the entropy and/or kurtosis of the respective wavelet coefficients is/are determined (step 48). Based on the subband-specific entropy and/or kurtosis value(s), the system then indicates whether epileptiform activity is present in the EEG signal (step 49).

As is discussed in the above-mentioned EP patent application, the normalized form of the k:th order central moment, where k is greater than two, can be calculated by dividing the k:th order central moment by the second order central moment raised to the power of k/2. The second order central moment is commonly known as the variance, whereas the normalized forms of the third and fourth order central moments are called skewness and kurtosis, respectively. Therefore, at least one measure may be determined based on the valid measurement data supplied to the further calculation stage, the at least one measure belonging to a measure set comprising a first measure indicative of the entropy of the said valid measurement data and a second measure indicative of a normalized form of k:th order central moment of the said valid measurement data, where k is an integer higher than three.

Figure 5:
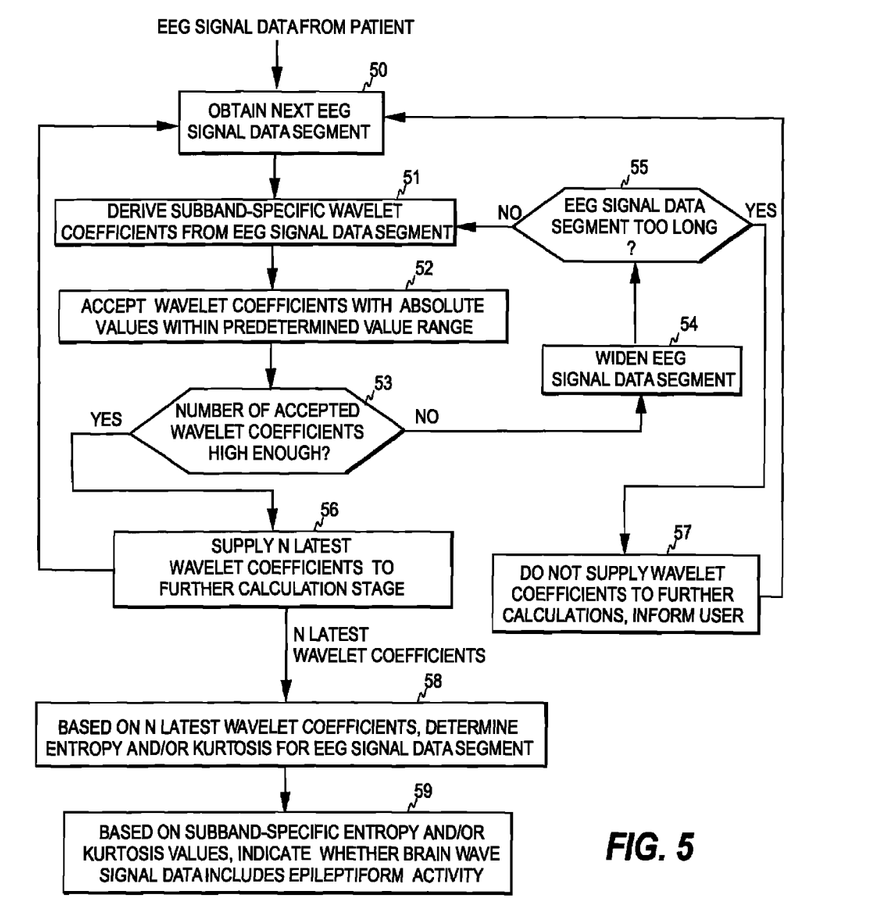
FIG. 5 is a flow diagram illustrating an embodiment in which the content of the set of valid measurement data is increased in steps, when the embodiment is applied in the context of monitoring epileptiform activity.

In the embodiments of FIGS. 3 and 4, the amount of valid measurement data in the set is increased continuously as new measurement data is obtained based on the incoming brain wave signal data. Therefore, the measurement data set may be supplied to the further processing stage at once when the amount of data in the set reaches the level required by the said further processing stage. In contrast to this embodiment, FIG. 5 illustrates another embodiment in which the amount of valid measurement data is increased in a stepwise manner. It is assumed in FIG. 5 that the mechanism is used in the context of monitoring epileptiform activity in EEG. In the embodiment of FIG. 5, a segment of EEG signal data is selected from the incoming EEG signal data (step 50). The length of the segment may be, for example, 5 seconds, and the segment typically includes the EEG signal samples obtained during the latest 5 seconds. As is common in the art, the digitized signal samples are processed as sets of sequential signal samples representing finite time blocks or time windows, commonly also termed "epochs". Subband-specific wavelet coefficients are calculated based on the signal samples of the data segment (step 51) and the coefficients fulfilling the threshold criteria are accepted (step 52). The number of accepted coefficients obtained from the EEG data segment is checked at step 53, and if the number is not high enough, the data segment is widened by a predetermined amount, such as 2 seconds (step 54). Next, the length of the widened segment is checked at step 55 to ascertain that the widened length does not exceed the maximum accepted segment length. If the data segment does not extend too far to the past, steps 51 and 52 are repeated for the widened EEG data segment.

In this way, the length of the EEG data segment is widened until a sufficient amount of acceptable wavelet coefficients is obtained from the segment at step 52 or until the length of the segment has reached the maximum accepted segment length, such as 15 seconds. In the latter case, the entropy and/or kurtosis of the time series of the wavelet coefficient is/are not determined and the user is informed of the situation (step 57). In the former case, N latest acceptable coefficients are supplied (step 56) to the further calculation stage, which may include steps similar to those discussed in connection with FIG. 4.

Figure 6:
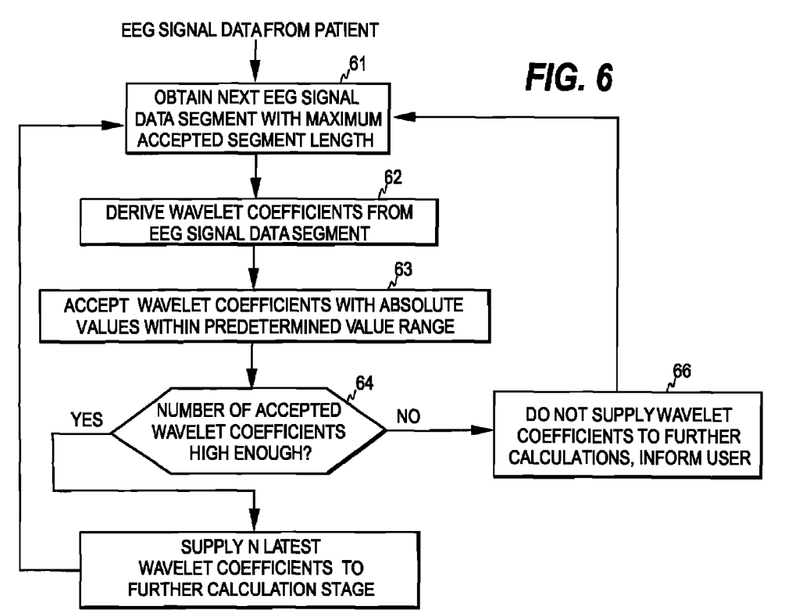
FIG. 6 illustrates a practical embodiment of the method of the invention.

In practice, the embodiment of FIG. 5 may be simplified by directly selecting an EEG signal data segment with maximum allowed segment length. This embodiment is illustrated in FIG. 6. Since an EEG signal data segment with maximum allowed segment length is selected directly from the incoming EEG signal data (step 60), there is no need to widen the segment length if the number acceptable coefficients obtained from the segment remains below the required level, but in that case the process may directly skip the calculation of entropy and/or kurtosis of the wavelet coefficients and inform the user of the situation (step 66).

As discussed above, the calculation of a single entropy and/or kurtosis value is adaptive in time, but fixed in the number of wavelet coefficients. In other words, to obtain a single entropy and/or kurtosis value, a data segment is employed, which is adaptive in time domain. However, a constant number of coefficients is produced as input data for the calculation, although part of the measurement data may be dropped.

Figure 7A:
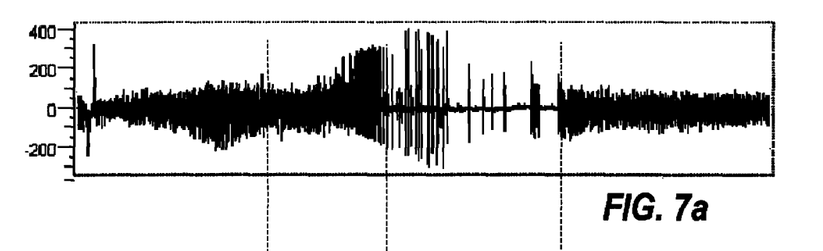
FIGS. 7a and 7b illustrate the performance of the mechanism of the invention in the context of monitoring epileptiform activity during epileptiform burst suppression periods.
Figure 7B:
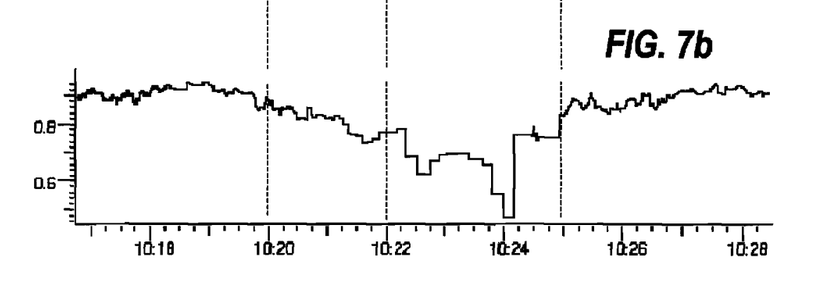

FIGS. 7a and 7b illustrate the performance of the mechanism of the invention in the context of detection of epileptiform activity during BS waveforms. FIG. 7a shows recorded EEG during deepening sevoflurane anesthesia. In this example, epileptiform activity starts around 10:20, while epileptiform burst suppression starts around 10:22 and ends around 10:25. FIG. 7b illustrates the entropy calculated according to the embodiment shown in FIG. 6. As can be seen from the figure, the entropy calculated behaves consistently even during BS waveforms and thus enables accurate monitoring of the epileptiform activity even during such waveforms of the EEG.

Figure 8:
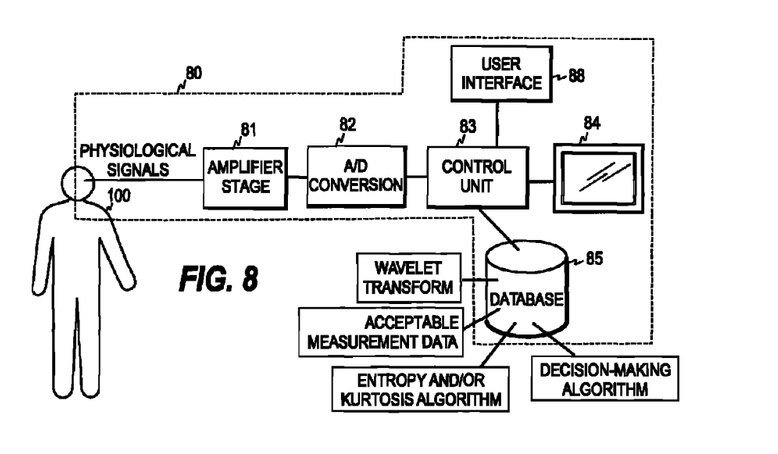
FIG. 8 illustrates one embodiment of the system of the invention.

FIG. 8 illustrates one embodiment of the system according to the invention. As mentioned above, the physiological signal data acquired from a patient is typically EEG signal data. The EEG signal is typically measured from the forehead of the patient 100, which is a preferred measurement site due to the ease of use of the measurement and the reduced inconvenience caused to the patient.

The signals obtained from the EEG sensors are supplied to an amplifier stage 81, which amplifies the signals before they are sampled and converted into digitized format in an A/D converter 82. The digitized signals are then supplied to a control unit 83 (including a microprocessor), which may then record the signals as an EEG time series.

The control unit is provided with a database or memory unit 85 holding the digitized physiological signal data obtained from the sensors. Before the actual processing of the physiological signal data, the control unit may perform various pre-processing phases for improving the quality of the data. The actual recording of the physiological signal data may thus occur in a conventional manner, i.e. the measurement device 80 including the above elements serves as a conventional measurement device. However, certain parameters may be set according to the requirements of the application in question. For example, if epileptiform activity is detected, the sampling frequency of the device may be selected so that the separated frequency band(s) correspond (s) to the epileptiform waveforms of interest.

Additionally, the control unit is provided with the above-described algorithms for processing the physiological signal data according to the invention and with the algorithms needed in the further processing stage, such as the algorithms for detecting epileptiform waveforms in brain wave signal data.

Figure 9:
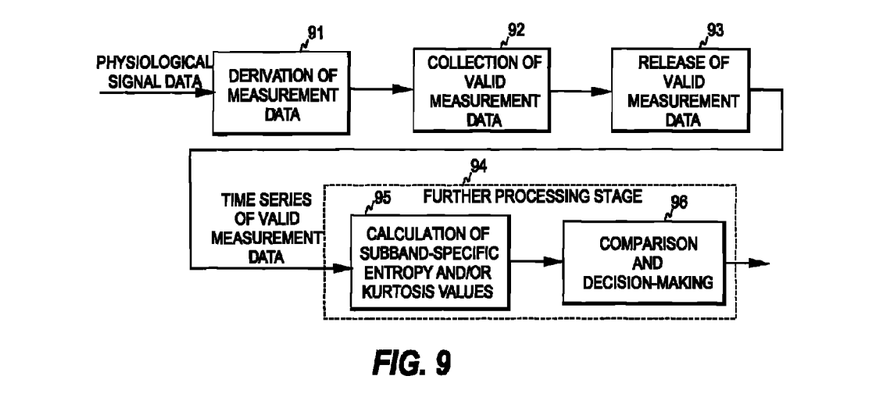
FIG. 9 illustrates the operational units of the control unit of FIG. 8 for detecting epileptiform activity in brain wave signal data.

As shown in FIG. 9, the control unit may thus include three successive operational modules or units: a first module 91 for deriving the measurement data from the time series of the physiological signal data, a second module 92 for selecting valid measurement data from among the measurement data derived, and a third module 93 for releasing the selected measurement data for the use of a further processing stage 94.

In case of detection of epileptiform activity, the first module typically includes a wavelet-based filter bank yielding a time series of wavelet coefficients, but may also include at least one filter yielding a time series of signal amplitude or signal power for the desired subband(s). In case of detection of epileptiform activity, the further processing stage may comprise, for example, a first sub-module 95 for calculating subband-specific entropy and/or kurtosis values based on the valid wavelet coefficients and a second sub-module 96 for comparing the subband-specific entropy and/or kurtosis values with corresponding thresholds and for making a decision on the presence of the respective waveforms in the EEG signal data. In a simplified embodiment of the invention, the second sub-module may also be an indicator module that presents the subband-specific entropy and/or kurtosis values to the user so that the user may deduce whether epileptiform waveforms of a specific type are present. Since entropy and kurtosis are continuous scale values, the method of the invention may be used for the quantification of the degree of epileptiform activity of the patient. This is useful for monitoring purposes, since the method is able to monitor both the development and the recovery of the epileptiform activity, as can be seen from FIGS. 7a and 7b. This allows, for example, monitoring of the effects of the treatment, such as the medication, of the patient.

Although one control unit (processor) may perform the calculations needed, the processing of the physiological signal data obtained may also be distributed among different processors (servers) within a network, such as a hospital LAN (local area network). For example, a conventional measurement device may record the physiological signal data and an external processor may be responsible for processing the data according to one of the embodiments described above.

The control unit may display the results of the application on the screen of a monitor 84 connected to the control unit. This may be carried out in many ways using textual and/or graphical information. The system further includes user interface means 88 through which the user may control the operation of the system.

As discussed above, brain wave data may also be acquired through a standard MEG recording. The measurement device 80 may thus also serve as a conventional MEG measurement device, although a MEG measuring arrangement is far more expensive than an EEG measuring arrangement. The software enabling a conventional EEG or MEG measurement device 80 to carry out the steps required by the application in question, such as detection of epileptiform waveforms, may also be delivered separately to the measurement device, for example on a data carrier, such as a CD or a memory card, or through a telecommunications network. In other words, a conventional measurement device may be upgraded by a plug-in unit that includes software enabling the measurement device to perform the analysis, such as detection certain epileptiform waveforms, based on the signal data it has obtained from the patient.

Since the method of the invention does not require high computation power, it may be used in various ambulatory devices, such as portable patient monitors, for carrying out the step of application concerned. The mechanism of the invention may also be introduced into various devices operating outside a clinical environment, such as mobile phones, PDA devices, or vehicle computers, which allows the application to be carried out during day-to-day activities.

The mechanism of the invention may also be utilized in off-line monitoring of the patient. In the context of off-line monitoring, it may also be adequate to perform the analysis based on a single set of valid measurement data. In other words, in off-line monitoring it may not be necessary to repeat the collection of valid measurement data for consecutive segments of the signal.

Although the invention was described above with reference to the examples shown in the appended drawings, it is obvious that the invention is not limited to these, but may be modified by those skilled in the art without departing from the scope and spirit of the invention. For example, the set of valid measurement data may be supplied to the further processing stage unconditionally, and if any of the supplied data is too old, the supplied data may be provided with an appropriate indication so that the device may indicate when the calculated result does not represent the current state of the patient.

The invention claimed is:

1. A method for suppressing the effects of suppression waveforms in patient monitoring, the method comprising:
    receiving a segment of a time series of brain wave signal data obtained from a patient;
    decomposing the segment into at least one predetermined subband using a processor;
    deriving measurement data from the predetermined subband using a processor, wherein the measurement data is a time series sequence of quantitative characteristics of the brain wave signal data within the predetermined subband;
    collecting valid measurement data from the derived measurement data, using a processor, by selecting measurement data that fulfills at least one predetermined threshold condition; and
    supplying at least a portion of the valid measurement data to a further processing stage when the amount of valid measurement data is at least at a predetermined level; and
    determining using a processor a first measure indicative of the entropy of the valid measurement data supplied to the further processing stage.

2. A method according to claim 1, further comprising repeating the deriving and collecting for consecutive segments of the time series, wherein the supplying is performed for at least some of the consecutive segments of the time series.

3. A method according to claim 2, wherein
    the decomposing step and the deriving step is performed continuously from the time series of the brain wave signal data as new values of the physiological signal data are received; and the supplying is performed upon the amount of valid measurement data reaching the predetermined level.

4. A method according to claim 1, wherein the predetermined subband is indicative of a specific type of epileptiform activity; and discriminating, based on the first measure, epileptiform brain wave signal data from non-epileptiform brain wave signal data.

5. A method according to claim 2, wherein the supplying includes supplying a fixed amount of valid measurement data for each of the at least some of the consecutive segments.

6. A method according to claim 5, wherein the supplying is omitted if the fixed amount includes valid measurement data corresponds to brain wave signal data that is older than a predetermined maximum time limit, and wherein the supplying is performed if the fixed amount fails to include valid measurement data corresponds to brain wave signal data that is older than a predetermined maximum time limit.

7. A method according to claim 1, wherein the deriving includes deriving measurement data from the segment, wherein the segment has a first predetermined length.

8. A method according to claim 7, further comprising repeating the deriving if the amount of valid measurement data collected from the measurement data derived from the segment remains below the predetermined level, wherein the repeated deriving includes widening the segment and deriving the measurement data from the widened segment of the time series.

9. A method according to claim 1, wherein the time series sequence of quantitative characteristics of the brain wave signal data comprises signal amplitude, signal power, or a wavelet coefficient within the predetermined subband.

10. A method according to claim 1, wherein the further processing stage includes determining, based on the valid measurement data supplied to the further processing stage, a second measure indicative of a normalized form of k:th order central moment of the valid measurement data supplied to the further processing stage, where k is an integer higher than three; and discriminating, based on the first measure and the second measure, epileptiform brain wave signal data from non-epileptiform brain wave signal data.

11. A method according to claim 1, wherein the collecting includes collecting measurement data whose values are within a predetermined value range.

12. The method of claim 1, wherein:
the measurement data comprises wavelet coefficients for the predetermined subband;
valid measurement data comprises wavelet coefficients greater than a lower threshold value and less than a higher threshold value; and
the first measure is indicative of the entropy of the valid measurement data.

13. An apparatus for suppressing the effects of suppression waveforms in patient monitoring, the apparatus comprising:
a first data processing unit configured to:
receive a segment of a time series of brain wave signal data obtained from a patient;
decompose the segment into at least one predetermined subband, and
derive measurement data from the predetermined subband, wherein the measurement data is a time series sequence of quantitative characteristics of the brain wave signal data within the predetermined subband;
a data collection unit configured to select, from among the derived measurement data, measurement data that fulfills at least one predetermined threshold condition, thereby to form a set of valid measurement data; and
a data release unit configured to supply at least a portion of the set of valid measurement data to a further processing unit, when the amount of valid measurement data in the set is at least at a predetermined level; and
the further processing unit configured to determine a first measure indicative of the entropy of the valid measurement data supplied to the further processing unit.

14. An apparatus according to claim 13, wherein the predetermined subband is indicative of a specific type of epileptiform activity; and
the further processing unit is further configured to discriminate based on the first measure, epileptiform brain wave signal data from non-epileptiform brain wave signal data.

15. An apparatus according to claim 13, wherein the data release unit is configured to supply a fixed amount of valid measurement data to the further processing unit.

16. An apparatus according to claim 15, wherein the data release unit is configured to supply the fixed amount of valid measurement data only if the fixed amount fails to include valid measurement data—corresponding to brain wave signal data that is older than a predetermined maximum time limit.

17. An apparatus according to claim 13, wherein
the first data processing unit is configured to decompose the segment into at least one subband and derive the measurement data continuously from the subband upon reception of new values of the physiological signal data; and
the data release unit is configured to supply the at least a portion of the set of valid measurement data in response to the amount of valid measurement data in the set reaching the predetermined level.

18. An apparatus according to claim 13, wherein the segment has a first predetermined length.

19. An apparatus according to claim 13, wherein the data collection unit is further configured to widen the segment from which the measurement data is derived.

20. An apparatus according to claim 13, wherein the time series sequence of quantitative characteristics of the brain wave signal data comprises signal amplitude, signal power, or a wavelet coefficient within the predetermined subband.

21. An apparatus according to claim 13, wherein the further processing unit is further configured to
determine, based on the valid measurement data supplied to the further processing unit, a second measure indicative of a normalized form of kith order central moment of the valid measurement data supplied to the further processing unit, where k is an integer higher than three; and
discriminate, based on the first measure and the second measure, epileptiform brain wave signal data from non-epileptiform brain wave signal data.

22. An apparatus for suppressing the effects of suppression waveforms in patient monitoring, the apparatus comprising:
first data processing means for deriving measurement data from a segment of a time series of brain wave signal data obtained from a subject, wherein the first data processing means is configured to decompose the brain wave signal data into at least one predetermined subband, wherein the measurement data is a time series sequence of a quantitative characteristic of the brain wave signal data within the predetermined subband, and wherein the measurement data is derived from the predetermined subband;

data collection means for selecting, from among the derived measurement data, measurement data that fulfills at least one predetermined threshold condition, thereby to form a set of valid measurement data;

data release means for supplying at least a portion of the set of valid measurement data to a further processing unit, when the amount of valid measurement data in the set is at least at a predetermined level; and the further processing means for determining, based on the valid measurement data supplied to the further processing means, a first measure indicative of the entropy of the valid measurement data supplied to the further processing means.

23. A computer program product in non-transitory computer readable medium for suppressing the effects of suppression waveforms in patient monitoring, the computer product comprising:

a first program code portion configured to derive measurement data from a segment of a time series of brain wave signal data obtained from a subject, wherein the first program code portion is configured to decompose the brain wave signal data into at least one predetermined subband, wherein the measurement data is a time series sequence of a quantitative characteristic of the brain wave signal data within the predetermined subband, and wherein the measurement data is derived from the predetermined subband;

a second program code portion configured to select, from among the derived measurement data, measurement data that fulfills at least one predetermined threshold condition, thereby to form a set of valid measurement data;

a third program code portion configured to supply at least a portion of the set of valid measurement data to a further processing unit, when the amount of valid measurement data in the set is at least at a predetermined level; and a fourth program code portion configured to determine, based on the valid measurement data supplied to the further processing unit, a first measure indicative of the entropy of the valid measurement data supplied to the further processing unit.

* * * * *